United States Patent [19]

Schwartz

[11] 3,990,144
[45] Nov. 9, 1976

[54] SUTURE CUTTER AND REMOVAL MEANS

[76] Inventor: Boris Schwartz, 400 Park Ave., Paterson, N.J. 07504

[22] Filed: Feb. 12, 1976

[21] Appl. No.: 657,554

Related U.S. Application Data

[62] Division of Ser. No. 592,087, June 30, 1975, Pat. No. 3,961,419.

[52] U.S. Cl. ................................ 30/123; 30/317; 30/DIG. 8
[51] Int. Cl.² ...................... A61B 17/32; B26B 3/00
[58] Field of Search ............... 30/124, 34.2, 123 R, 30/DIG. 8, 317

[56] References Cited
UNITED STATES PATENTS

| | | | |
|---|---|---|---|
| 117,588 | 8/1871 | Woods | 30/DIG. 8 |
| 709,917 | 9/1902 | Marshall | 30/DIG. 8 |
| 1,477,510 | 12/1923 | Martin | 30/DIG. 8 |
| 1,829,577 | 10/1931 | Anderson | 30/124 |
| 2,556,366 | 6/1951 | Miller | 30/299 X |
| 2,705,833 | 4/1955 | Grantz | 30/DIG. 8 |
| 2,733,507 | 2/1956 | Dangelo | 30/123 X |
| 2,913,822 | 11/1959 | Wallbillich | 30/294 |
| 3,600,806 | 8/1971 | Naccash | 30/294 |
| 3,624,683 | 11/1971 | Matles | 30/124 |
| 3,879,846 | 4/1975 | Allen | 30/124 |

FOREIGN PATENTS OR APPLICATIONS

| | | | |
|---|---|---|---|
| 588,195 | 5/1947 | United Kingdom | 30/289 |
| 359,240 | 10/1931 | United Kingdom | 30/123 |

*Primary Examiner*—Al Lawrence Smith
*Assistant Examiner*—J. T. Zatarga
*Attorney, Agent, or Firm*—Ralph R. Roberts

[57] ABSTRACT

An inexpensive suture cutter is shown in which the cutting portion is a sharpened edge of a wire-like member one-eighth inch or less in diameter at the cutting portion. This wire-like cutting portion has a blunt end to prevent accidental penetration of the skin as the knife portion of the cutter is slid under the sutures which are then cut as the cutting edge is slid along and underneath the sutures. Prior to cutting a length of adhesive tape is placed on and secured to the sutures to be cut and removed. The edge of the tape is placed adjacent or over the proposed cutting path. The sutures are removed by and when the tape is lifted from the skin after the sutures have been severed by the cutter.

3 Claims, 5 Drawing Figures

SUTURE CUTTER AND REMOVAL MEANS

CROSS REFERENCE TO RELATED APPLICATION

This application is a divisional application by Boris Schwartz of his application, Ser. No. 592,087, filed June 30, 1975 and entitled. "Suture Cutter and Method of Removal", now U.S. Pat. No. 3,961,419 dated June 8, 1976. Restriction was required by the Examiner of this application in his Action dated November 17, 1975.

BACKGROUND OF THE INVENTION

1. Field of the Invention

With reference to the classification of art as established in the United States Patent and Trademark Office the present invention is found in the general Class entitled, "Cutlery" (Class 30) and in the subclass thereunder entitled, "combined with material holder or disposal" (subclass 124) and in the subclass entitled, "razors-combined with means to lift hair or skin" (subclass 34.2).

2. Description of the Prior Art

The removal of stitches from incisions is generally performed by a doctor and/or medical assistant. The sutures are generally cut and removed by the use of special sissors and forceps or tweezers by which the cut suture may be grasped and pulled from the healed incision. The present invention has for this purpose an apparatus and method which provides an inexpensive improvement for the cutting and removal of sutures. The present invention contemplates an inexpensive cutter constructed of wire with an end of the wire curved and formed to provide a finger gripping and manipulative portion. This wire-like suture cutting device is made of low carbon steel. This cutter is used with a given length of adhesive gauze or the like. The suture cutter and the gauze are both inexpensive and it is proposed and contemplated that these will be discarded after use. This wire-like cutter, although it has a sharp edge sufficient for cutting several sutures, is not contemplated to have a sustaining sharp edge as the cutter will be discarded after this one use.

An attempt to provide a combination suture cutter and remover is found in U.S. Pat. No. 3,879,846 as issued on Apr. 29, 1975 to ALLEN, JR. which provides a combination implement for cutting and removing surgical sutures consisting of a portion forming a forceps and a longitudinal suture cutting element extending between the arms of the forceps an anchored to one arm and the bight of the forceps body. This device requires a tweezer grasping action to lift and pull the suture. The very low profile cutting blade of this application with its immediate severing action is not shown in this or other known prior art. The sliding cut employed by this cutter minimizes the effort to cut the sutures and the tape used to lift and remove the cut sutures is easily manipulated.

SUMMARY OF THE INVENTION

This invention may be summarized at least in part with reference to its objects.

It is an object of this invention to provide a method of suture removal which is not only inexpensive and can be performed without assistance by the surgeon but is also very rapid. This method is quite convenient for both the patient and for the one removing the sutures. It is contemplated that the suture cutter be made of small diameter wire and have a short portion formed with a small cutting edge and a blunt entering end. This cutting portion in use is slid underneath the suture and as the sharp edge is slid along a path transverse to the suture the suture is cut. To assist in removing the sutures which customarily are pulled from the skin by tweezers, forceps and the like it is contemplated that a length of adhesive tape or adhesive coated material be placed upon the uncut sutures prior to their being cut. As the suture is severed the tape is lifted from the skin and with the severed suture adhered to the tape is pulled from the skin. After the tape and the attached sutures are removed from the skin of the patient the tape and the cutter are discarded.

The suture cutter, to be hereinafter more fully described, resembles a large paper clip with one of the legs of the clip partially pulled from the original configuration, this leg portion is formed with a knife-like edge.

It is a further object of this invention to provide, and it does provide, an inexpensive suture cutter and removal apparatus which is contemplated to have a one time use. A cutter made of wire of one-eighth inch diameter or less may be shaped much like a common large paper clip. One of the legs of this wire form is formed with a sharp edge and the end is blunt to prevent skin penetration at the time of suture cutting. With this cutter is provided a length of adhesive tape which is pressed onto the skin and sutures before cutting. One end of the tape is then lifted sufficiently for the entrance of the cutting portion of the cutter which is slid under the suture and then advanced to cut the suture. As the cutter is advanced the tape is lifted to enable the sutures to be sequentially cut until all are cut after which the tape and adhered sutures are removed and discarded.

In addition to the above summary the following disclosure is detailed to insure adequacy and aid in understanding of the invention. This disclosure, however, is not intended to cover each variation in form or additions of further improvements. For this reason there has been chosen a specific embodiment of the cutter and adhesive tape strip as adopted for use in removing cut sutures and showing a preferred means for apparatus and method. This specific embodiment has been chosen for the purpose of illustration and description as shown in the accompanying drawing wherein:

Figure 1:
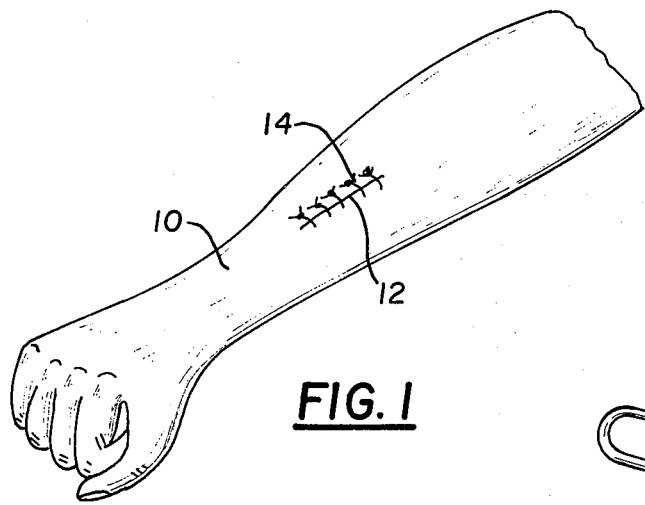
FIG. 1 represents an arm of the patient and showing sutures as used to close a cut.
Figure 3:
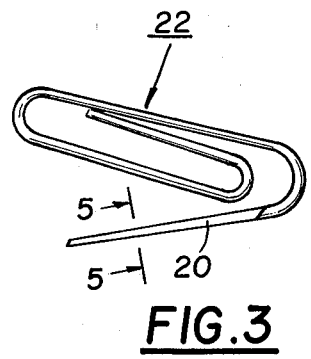
FIG. 3 represents a side view of a suture cutter in substantially a full size.

In the following description and in the claims the details are identified by specific names for convenience; these names, however, are intended to be generic in their application. Corresponding reference characters refer to like members throughout the figures of the drawing. The drawing and specification disclose pertinent details but it should be understood that structural details may be modified and that the suture cutter may be incorporated in other structural forms than shown.

DESCRIPTION OF THE SUTURE CUTTER AND METHOD OF REMOVING CUT SUTURES

Figure 2:
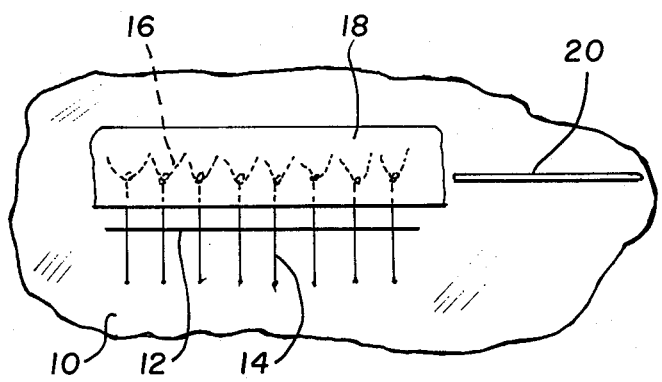
FIG. 2 represents an enlarged view of a cut closed with a series of spaced sutures and an adhesively coated tape placed over a portion of the sutures and indicating a proposed path of the cutting blade portion of the suture cutter prior to the cutting of the sutures.

Referring now in particular to the drawing, there is shown a typical representation of the suturing of a cut on an arm 10 of a patient having a cut 12 closed for healing by a plurality of sutures 14. These sutures are inserted and tied in the normal manner and as is customary the positioning and spacing are neatly arranged. In FIG. 2 is shown in an enlarged view the typical arm 10 having a cut 12 closed by a plurality of sutures 14. It is anticipated that the knotted portions of the sutures, which are indicated as 16, may lay more-or-less in a straight line in which case an adhesive tape 18 is placed over these suture knots to tightly adhere the knots and adjacent suture portions to the adhesive side of the tape. Preferably this tape has an adhesive coating as is adapted for ready disengagement from skin. This is the adhesive preferable for use with the tape 18. With the placement of the adhesively surfaced tape on the sutures the knife cutting portion 20 of the suture cutter, generally indicated as 22, is brought to the sutured area.

USE OF SUTURE CUTTER AND METHOD OF REMOVING CUT SUTURES

Figure 4:
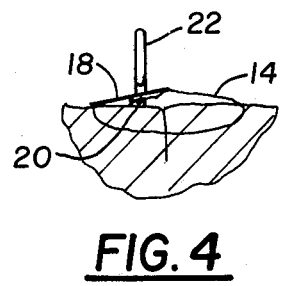
FIG. 4 represents in an enlarged scale a sectional view showing the placement of the cutting edge of the suture cutter in relation to a typical suture and of the tape used to achieve a lifting and removal of the cut suture.
Figure 5:
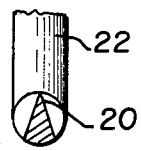
FIG. 5 represents an enlarged view taken on the line 5—5 of FIG. 3 and showing the construction of the cutting portion of the suture cutter.

To use the apparatus of this invention the surgeon or attendant lifts one end portion of the affixed tape 18 sufficiently for the blunt end and cutting portion 20 to be brought to and under the suture as in FIG. 4. The knife portion is then advanced with a slight upward urging of the blade so as to slice the suture as the cutting edge portion is advanced forward. In the meantime, the tape is lifted sufficiently for the cutting portion to slide under the next suture. As progressively the sutures are cut, the tape at these cut sutures is lifted. This method enables all the sutures to be cut in a sequential manner. After all the sutures are cut the adhered cut sutures and tape are pulled from the skin and the now removed sutures and tape are discarded. If these are the only sutures to be removed at this time it is contemplated that the suture cutter will also be discarded.

It is to be noted that the suture cutter is made of a relatively low carbon steel wire and as a knife has no other use or dangerous potential. The cost of such a suture cutter made in large quantities can be produced for one or two cents or less if the cutting edge portion 20 is made by an automatic swaging or shaping action. Since this is a one time use of a product, after the shaping of the edge the suture cutter as a whole may be lightly washed-plated or lightly coated prior to its being sealed in a package for storage and shipment. The cost of such treating of the steel member is only a few cents per thousand.

The invention includes the placing of an adhesively coated tape-like member over a series of sutures with the exposed suture portions embedded in the adhesive portion of the tape. The tape is progressively lifted as the sutures are cut. Cutting of the sutures is achieved by a forward slicing action. A cutting portion is formed on a steel wire of less than one-eighth of an inch in diameter. As reduced to practice, the preferred wire diameter of one-sixteenth of an inch is formed with a sharpened edge and a blunt forward end. A portion of the wire is formed into a loop-like configuration to provide a small manipulative handle.

Terms such as "left", "right", "up", "down", "bottom", "top", "front", "back", "in", "out" and the like are applicable to the suture cutter and tape as shown and described in conjunction with the drawing. These terms are merely for the purposes of description and do not necessarily apply to the position in which the cutter and tape may be placed on the patient or may be constructed or used.

While a particular embodiment of the cutter and tape and the removal of sutures thereby have been shown and described it is to be understood modifications may be made within the scope of the accompanying claims and protection is sought to the extent the prior art allows.

What is claimed is:

1. A suture cutter and removing instrument which is of inexpensive metal wire construction permitting and encouraging the discarding of the instrument after a one time use, said instrument including: (a) a cutting blade portion of the instrument, the cutting blade portion being formed as a relatively straight blade portion at and including the entering tip of the instrument and including the tip having a height not generally exceeding the diameter of the wire, the cutting blade portion being treated so as to have a hardness of generally less than fifty Rockwell "C", the cutting blade portion having a top edge extending from the entering tip and a short distance therefrom and sufficiently sharp so as to sever surgical sutures when the cutting blade portion is brought underneath the suture and while in tensioned engagement with the suture the cutting blade portion is slid thereacross and upwardly to effect a cutting of the suture; (b) a blunt end formed at said tip of the cutting blade portion, this blunt end being configured so as to make accidental penetration of the skin difficult, and (c) a handle formed from the same wire which is bent into an elongated loop similar to those provided in a paper clip, the handle positioned adjacent the cutting blade portion so as to define an acutely angled V-form with the handle above the said top edge when in the cutting condition, the handle so formed providing means for grasping the handle to manipulate the entering cutting blade portion so as to guide and slide the tip of the cutting blade portion under and across the sutures and as an assist for the removal of the cut sutures there is placed on the uncut sutures a length of flexible tape-like material having one surface coated with an adhesive of sufficient adhesion to entrap, retain and pull from the skin of a patient the sutures as they are cut and after said length of tape has been pressed into retaining engagement with the uncut sutures prior to their being severed by the cutting blade portion of the instrument and as the cut sutures are removed from the skin by the lifting of the tape from the skin the cutting blade portion is moved under the remaining sutures until all are severed and removed.

2. Suture cutting and removing instrument as in claim 1 in which the cutting edge is formed as by swaging.

3. Suture cutting and removing instrument as in claim 1 in which the wire form is protected against rust and the like by at least a thin plating.

* * * * *